(12) United States Patent
Stubbs et al.

(10) Patent No.: US 7,494,456 B2
(45) Date of Patent: Feb. 24, 2009

(54) TISSUE POSITIONING SYSTEMS AND METHODS FOR USE WITH RADIATION THERAPY

(75) Inventors: James B. Stubbs, Alpharetta, GA (US); Rance A. Winkler, Miramar, FL (US)

(73) Assignee: CYTYC Corporation, Marlborough, MA (US)

( * ) Notice: Subject to any disclaimer, the term of this patent is extended or adjusted under 35 U.S.C. 154(b) by 858 days.

(21) Appl. No.: 10/897,382

(22) Filed: Jul. 22, 2004

(65) Prior Publication Data

US 2005/0085681 A1 Apr. 21, 2005

Related U.S. Application Data

(63) Continuation of application No. 09/882,506, filed on Jun. 15, 2001, now Pat. No. 6,673,006, and a continuation-in-part of application No. 10/750,921, filed on Dec. 31, 2003.

(51) Int. Cl.
*A61N 5/00* (2006.01)
(52) U.S. Cl. .......................................................... 600/3
(58) Field of Classification Search .................. 600/1–8
See application file for complete search history.

(56) References Cited

U.S. PATENT DOCUMENTS

| | | |
|---|---|---|
| 3,872,856 A | 3/1975 | Clayton |
| 4,665,906 A | 5/1987 | Jervis |
| 4,706,652 A | 11/1987 | Horowitz |
| 4,754,745 A | 7/1988 | Horowitz |
| 5,422,926 A | 6/1995 | Smith et al. |
| 5,429,582 A | 7/1995 | Williams |
| 5,484,384 A | 1/1996 | Fearnot |
| 5,562,594 A | 10/1996 | Weeks |
| 5,724,400 A | 3/1998 | Swerdloff et al. |
| 5,800,333 A | 9/1998 | Liprie |
| 5,803,895 A | 9/1998 | Kronholz et al. |
| 5,851,182 A | 12/1998 | Sahadevan |
| 5,863,284 A | 1/1999 | Klein |
| 5,913,813 A | 6/1999 | Williams et al. |
| 6,036,631 A | 3/2000 | McGrath et al. |

(Continued)

FOREIGN PATENT DOCUMENTS

EP 0867200 9/1998

(Continued)

OTHER PUBLICATIONS

Ravinder, Nath et al. "Development of an[241] Am Applicator For Intracavitary Irradiation of Gynecologic Cancers", I.J. Radiation Oncology, Biology, Physics, vol. 14, No. 5, (1988).

*Primary Examiner*—John P Lacyk
(74) *Attorney, Agent, or Firm*—Heather Larson

(57) ABSTRACT

A brachytherapy device including a spacing member is disclosed herein. The spacing member is useful in that the instrument is effective to limit the amount of radiation that comes into contact with the sensitive tissue, and thereby protect sensitive tissue from overheating or hotspots, and/or protect against radiation exposure outside of the patient's body which may affect healthcare providers or others who might come close to the patient. In particular, the spacing apparatus is effective to control the proximity of a brachytherapy device to the outer surface of the sensitive tissue proximate to a surgical excision site.

11 Claims, 11 Drawing Sheets

U.S. PATENT DOCUMENTS

| | | |
|---|---|---|
| 6,066,856 A | 5/2000 | Fishman |
| 6,159,207 A | 12/2000 | Yoon |
| 6,616,629 B1 * | 9/2003 | Verin et al. ............ 604/101.05 |

FOREIGN PATENT DOCUMENTS

| | | |
|---|---|---|
| WO | 9719723 | 6/1997 |
| WO | 9911325 | 3/1999 |
| WO | 9933515 | 7/1999 |
| WO | 9942163 | 8/1999 |
| WO | 0074573 | 12/2000 |

\* cited by examiner

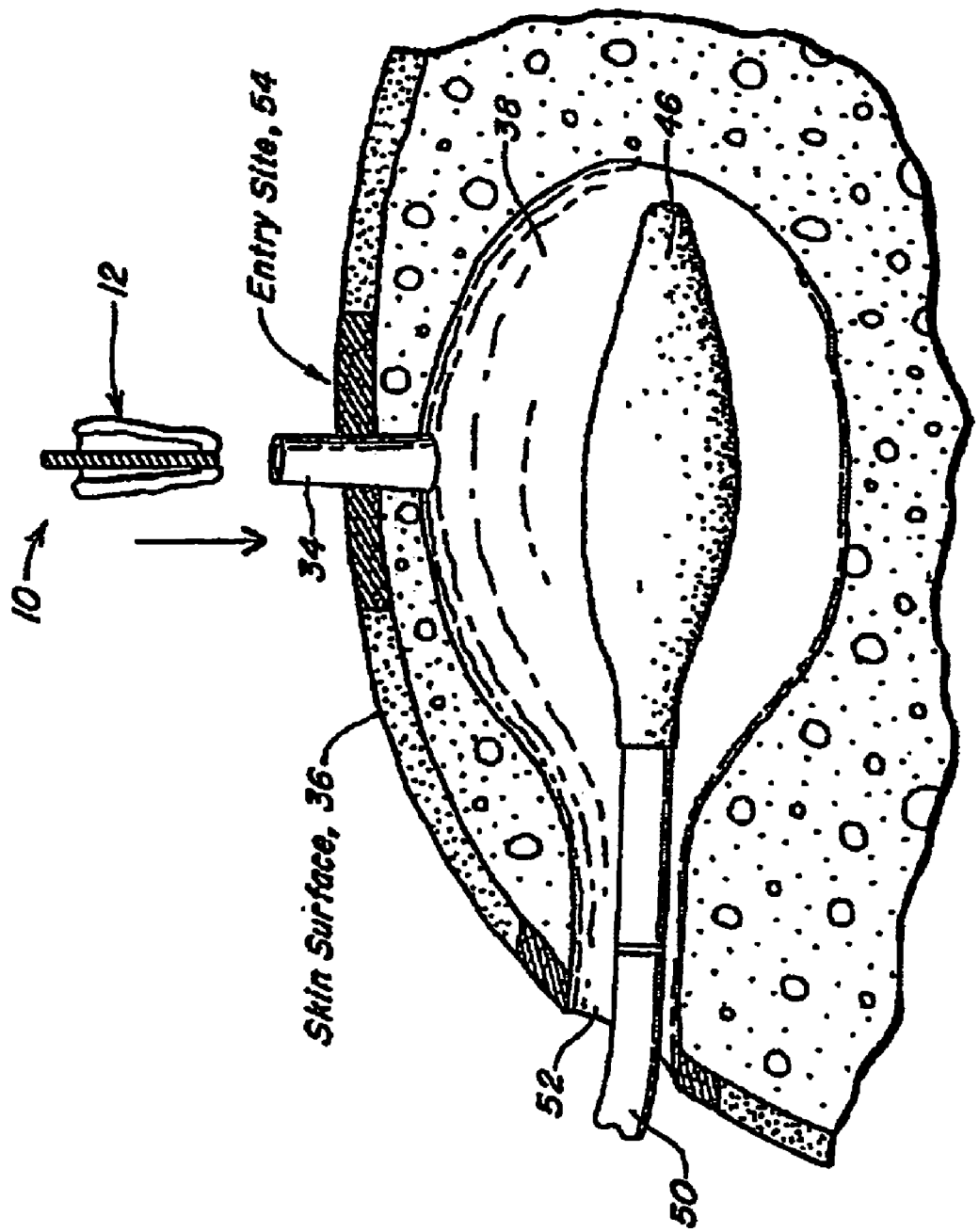

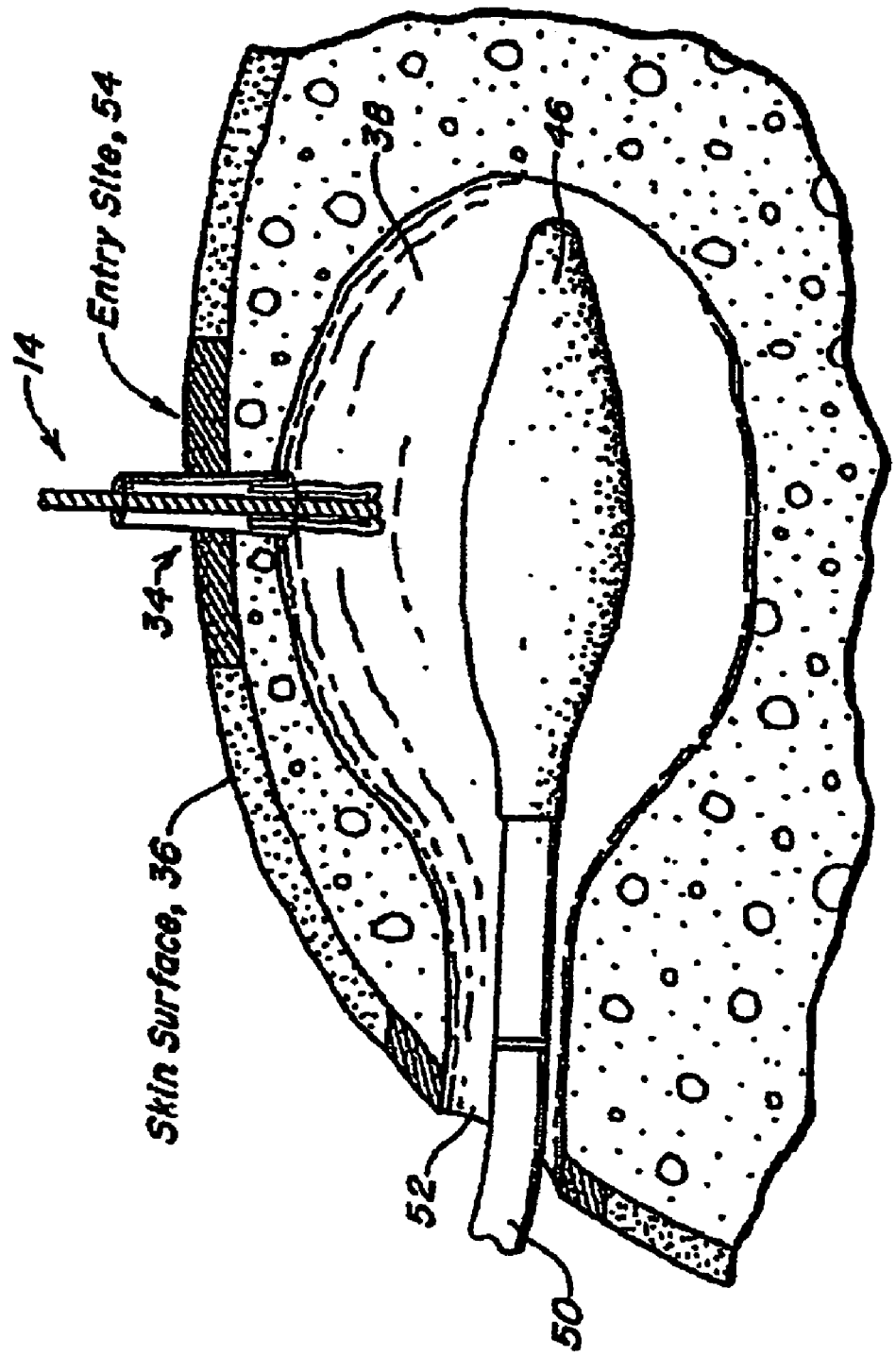

TISSUE POSITIONING SYSTEMS AND METHODS FOR USE WITH RADIATION THERAPY

CROSS-REFERENCE TO RELATED APPLICATIONS

This application is a continuation-in-part of co-pending U.S. patent application Ser. No. 10/750,921, filed Dec. 31, 2003; which is a continuation of U.S. patent application Ser. No. 09/882,506, filed Jun. 15, 2001, now U.S. Pat. No. 6,673,006. The contents of both Applications are incorporated herein by reference.

FIELD OF THE INVENTION

The present invention relates to methods and apparatus for use in treating proliferative tissue disorders, and more particularly to methods and apparatus for protecting sensitive tissue during radiation therapy.

BACKGROUND OF THE INVENTION

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary brachytherapy. The term "brachytherapy," as used herein, refers to radiation therapy delivered by a spatially confined radioactive material inserted into the body at or near a tumor or other proliferative tissue disease site. Owing to the proximity of the radiation source, brachytherapy offers the advantage of delivering a more localized dose to the target tissue region.

Brachytherapy can be performed by implanting radiation sources directly into the tissue to be treated. Interstitial brachytherapy is traditionally carried out using radioactive seeds such as $^{125}$I seeds. These seeds, however, produce inhomogeneous dose distributions. In order to achieve a minimum prescribed dosage throughout a target region of tissue, a large number of seeds must be used, resulting in very high doses being delivered to tissue in proximity to the seed, which can cause radionecrosis in healthy tissue.

An alternative method of performing post-surgical brachytherapy is the implantation or insertion of an inflatable balloon catheter system into the resection cavity. For example, U.S. Pat. No. 5,913,813 (which is hereby incorporated by reference in its entirety) discloses a double-wall balloon catheter including a balloon, or distensible reservoir, that can pushing tissues away from close proximity to a radiation source. This allows the irradiated tissue to be in a region of shallow dose gradient and results in a reduced risk of "hotspots" and radionecrosis.

In general, the amount of radiation desired by the physician is a certain minimum amount that is delivered to a region up to about two centimeters away from the margin of the excised tumor. It is desirable to keep the radiation that is delivered to the tissue in the target treatment region within a narrow absorbed dose range to prevent over-exposure to tissue at or near the radiation source, while still delivering the minimum prescribed dose at the maximum prescribed distance from the radiation source. It is also desirable, at least in some applications, to provide these advantages while tailoring the radiation dosage to avoid fully dosing sensitive tissue or to reduce the amount of radiation that escapes the patient's body.

Thus, there is a need for an instrument which can be used to deliver radiation from a radioactive source to target tissue within the human body with a desired intensity and at a predetermined distance from the radiation source without over-exposure of sensitive body tissues, such as skin or organ tissue for example, disposed proximate to the radiation.

SUMMARY OF THE INVENTION

The present invention provides a radiation device with a positioning or spacing member, and methods of use for positioning a radiation source at a distance apart from sensitive tissue. The spacing member is useful in that it is effective to limit the amount of radiation that comes into contact with the adjacent tissue, and thereby protect sensitive tissue from receiving more radiation than it can tolerate safely, and/or protect against radiation exposure outside of the patient's body which may affect healthcare providers or others who might come close to the patient.

The spacing member can have any shape and size, but is preferably adapted to provide a sufficient amount of space, hereinafter referred to as the desired spacing, between a radiation source within a brachytherapy device and adjacent tissue. For example, the spacing member may space sensitive tissue from a radiation source within a brachytherapy device. The desired spacing is preferably adapted to prevent damage to healthy tissue cells, while allowing cancerous cells to be destroyed. The spacing member can be mated to or disposed in conjunction with a brachytherapy device, or alternatively, can be formed as an integral part of a brachytherapy device.

In one embodiment, the spacing member is formed from an expandable balloon member. In the closed, deflated position, the balloon member is disposed or folded around an insertion member to allow the insertion member to be inserted through an opening, e.g. an introducer sheath, into a surgical excision site. Once inserted, the balloon member can be inflated to the open position to provide a predetermined amount of space between a radiation source and the tissue surrounding the surgical excision site. The necessary spacing is preferably equal to the height of the spacing member which is predeterminable—that is, the height can be fixed and predetermined, or the spacing member can be of a variable height that is selectable in use. The balloon member can have a preformed shape such that, when inflated, the balloon member is effective to provide the necessary spacing between the radiation device and the adjacent tissue.

In other aspects of the invention, a brachytherapy device is provided having an insertion member with proximal and distal ends, a first expandable balloon disposed on the distal end of the insertion member, and a spacing member disposed on the distal end of the insertion member proximal to the first expandable balloon. The expandable balloon is effective to receive a radiation source for treating target tissue surrounding a surgical excision site, and the spacing member is effective to position the expandable balloon at a distance apart from tissue surrounding an excision site.

In one such embodiment, the spacing member is a second expandable balloon adapted for spacing tissue from the first expandable balloon. For example, a brachytherapy device may include proximal and distal expandable balloons that are separately inflatable and adapted for different functions (i.e., spacing and containing a radiation source).

In an alternative embodiment, a single expandable balloon includes both a spacing member and a radiation containing portion. For example, a brachytherapy device can include an expandable surface member having multiple lobes. In use, one lobe can provide tissue spacing and space sensitive tissue from the other lobe which contains a radiation source.

In yet another embodiment, an asymmetric portion of an expandable surface member can act as the spacing member. For example, a generally cylindrically shaped expandable surface member can include a outwardly positioned asymmetric spacing area which does not conform to the generally cylindrical shape. In use, the asymmetric spacing area can provide increased spacing to sensitive tissue. For example, the asymmetric area can space tissue from a radiation source positioned within the expandable surface member such that the spaced tissue receives a radiation dose less than an isodose received by tissue adjacent to the cylindrically shaped portion of the expandable surface member.

In yet a further embodiment, the expandable surface member includes an asymmetric shape such that the asymmetric spacing area provides reduced spacing between tissue adjacent to the asymmetric spacing area and a radiation source position within the expandable surface member. One such exemplary asymmetric spacing area includes an inwardly positioned asymmetric spacing area that does not conform to the generally uniform shape of the expandable surface member.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 7A illustrates a brachytherapy device disposed within a surgical excision site, and a spacing member according to one embodiment of the present invention prior to insertion into the surgical excision site;

FIG. 7B illustrates the spacing member shown in FIG. 5A partially inserted into the surgical excision site;

FIG. 7D illustrates a brachytherapy device positioned at a distance apart from tissue disposed adjacent a surgical excision site by the spacing member of FIG. 5A, which is shown extended into an open position.

DESCRIPTION OF THE INVENTION

Figure 1A:
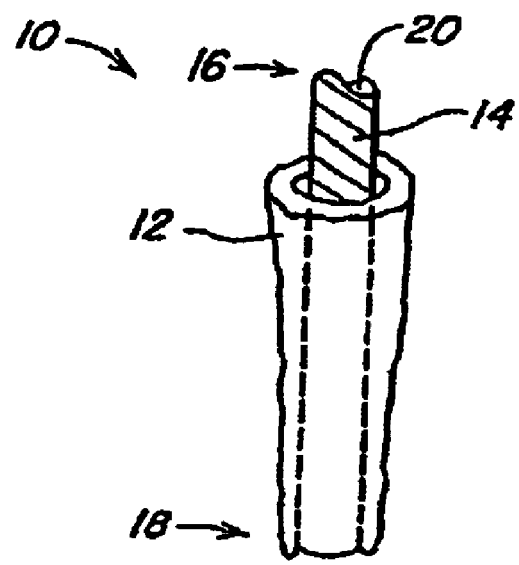
FIG. 1A is perspective view of a spacing member according to one embodiment of the present invention.

The present invention relates to methods and apparatus for controlling the proximity of a radiotherapy source to sensitive tissue. Ideally, radiation therapy makes use of the inherent difference in radiosensitivity between tumor cells and the adjacent normal tissues cells to destroy cancerous tissue while causing minimal disruption to surrounding normal tissues. At high doses of radiation, the percentage of exposed cells that survive treatment decreases with first-order kinetics in proportion to increasing radiation dose. With increasing cell death comes increasing risk of necrosis or tissue death in healthy tissue that is treated with a high dose of radiation.

Accordingly, the present invention provides a spacing member, and methods of use for positioning a radiotherapy source, such as a radiation source within a brachytherapy device, at a distance apart from sensitive tissue. The instrument is effective to limit the amount of radiation that comes into contact with the adjacent tissue, and thereby protect sensitive tissue from hotspots, and/or protect against radiation exposure outside of the patient's body which may affect healthcare providers or others who might come close to the patient.

The term "brachytherapy device" as used herein is intended to refer to radiation therapy delivered into the body at or near a tumor or other proliferative tissue disease site. A person of skill in the art will appreciate that such brachytherapy devices can use a variety of radiation sources, such as for example radioisotopes, miniature X-ray emitters (miniature X-ray tubes), and other radiation sources which can be positioned in conjunction with a brachytherapy device. Exemplary radioisotopes can include beta-emitters, gamma-emitters, and X-ray emitters. For example, if the radioisotope is a beta-emitter, it may be selected from the group consisting of $^{90}Y$, $^{188}Re$, $^{32}P$, $^{186}Re$, $^{106}Rh$, and $^{89}Sr$; if the radioisotope is a gamma-emitter, it may be selected from the group consisting of $^{60}Co$, $^{137}Cs$, and $^{192}Ir$; or if the radioisotope is an X-ray emitter, it may be selected from the group consisting of $^{103}Pd$, $^{109}Cd$, $^{145}Sm$, $^{149}Pm$, $^{169}Yb$, and $^{125}I$.

A non-limiting example, of a brachytherapy device suitable for use with the spacing member of the present invention is disclosed in U.S. Pat. No. 6,413,204, filed Apr. 15, 1999, and entitled "Interstitial Brachytherapy Apparatus and Method for the Treatment of Proliferative Tissue Diseases," which is hereby incorporated by reference in its entirety. In addition, this application provides detailed information on the effects of spacing on radiation dosing. While the aforementioned application provides examples of a brachytherapy device useful with the invention described herein having an outer expandable surface (such as an inflatable balloon for example) with a radiation source disposable inside the surface, a person of ordinary skill in the art will understand that other brachytherapy device configurations may be used within the spirit of the present invention.

A person skilled in the art should also appreciate that the spacing provided by the spacing member of the present invention is not limited to positioning and spacing brachytherapy devices. The disclosed spacing member may be used to position any type of radiation device or other medical device at a distance apart from tissue surrounding a surgical site.

In general, the spacing member according to the present invention can have a variety of shapes and sizes, and is preferably adapted to provide a sufficient amount of space, hereinafter referred to as the desired spacing, between the radiation source and sensitive tissue. The desired spacing is preferably adapted to prevent damage to healthy tissue cells, while allowing cancerous tissue to be destroyed.

The spacing member can provide the desired spacing with a number of different embodiments. In one exemplary embodiment, the spacing member can be a separate structure for disposing in conjunction with a brachytherapy device. Alternatively, the spacing member can be mated to, or formed with, a portion of the brachytherapy device. For example, the spacing member can be mated with a catheter member or balloon member of a brachytherapy device, or in yet another embodiment, the spacing member can be formed integrally with the balloon member of a brachytherapy device.

Figure 1B:
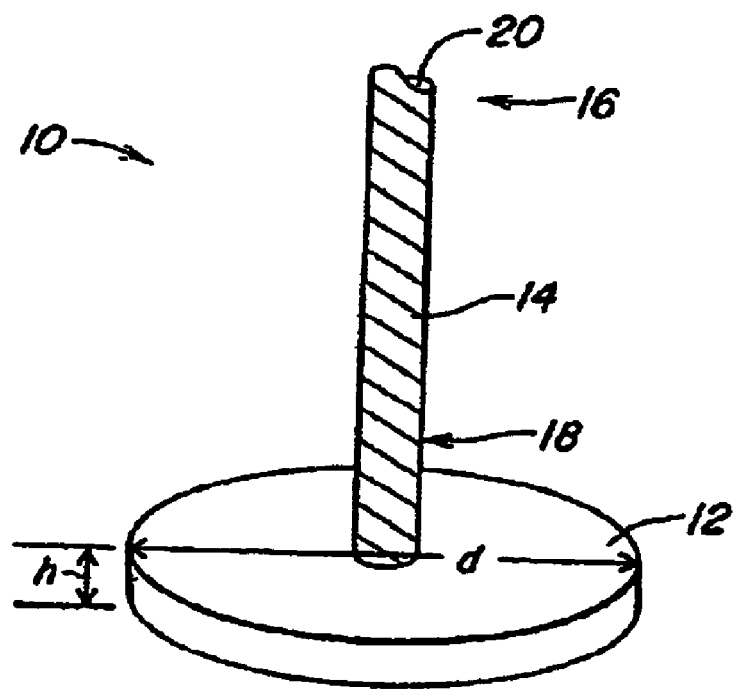
FIG. 1B is a perspective view of the spacing member of FIG. 1A in an open, extended position.

FIGS. 1A and 1B illustrate one embodiment of a device 10 including a spacing member 12 for use with a separate brachytherapy device. In general, the device includes a spacing member 12 and an elongate insertion member 14 having a proximal end 16 and a distal end 18. The elongate member 14 can optionally include an inner lumen 20, and can be a catheter, introducer sheath, or similar device. The spacing member 12 can be disposed within the inner lumen 20, disposed on or mated to a portion of the distal end 18 of the elongate member 14, or alternatively, can be formed integrally with the elongate member 14.

As shown in FIG. 1B, the spacing member 12 is substantially disk-shaped and includes a height h. The height h defines the desired spacing between the adjacent tissue and the brachytherapy device. The height h can be determined based on the amount of radiation being provided, and the distance between the radiation source and the tissue surrounding the excision site. While the spacing member can have any height h, preferably, the height is between about 1 and 5 millimeters, and more preferably is about 3 millimeters.

FIG. 1B also illustrates the spacing member 12 having a diameter d, which extends in a direction substantially perpendicular to the elongate member 14. The diameter d of the spacing member can vary, but is preferably determined based upon the intended use of the spacing member. For example, the spacing member can be adapted to protect or shield a particular area of tissue, and therefore the diameter can be determined based upon the amount of surface area to be protected and the configuration of the brachytherapy device. Preferably, the diameter d is between about 20 and 60 millimeters, and more preferably is about 40 millimeters.

While FIG. 1B illustrates a substantially disk-shaped spacing member 12, a person having ordinary skill in the art will appreciate that the spacing member 12 can have any shape, such as square, oval, rectangular, etc. In addition, diameter dimension d of the spacing member could represent any major dimension of a non-disk-shaped spacing member other than its height.

In use, the spacing member 12 can be movable between a closed position, shown in FIG. 1A, wherein the spacing member 12 is substantially disposed around the elongate member 14, and an open or deployed position shown in FIG. 1B, wherein the spacing member 12 is extended outward from the elongate member 14 in a direction substantially perpendicular to the elongate member 14. As shown in FIG. 1A, the spacing member 12 is disposed upward toward the proximal end 16 of the elongate member 14 to prevent the spacing member 12 from opening during insertion through an introducer sheath (not shown). This can be accomplished by a variety of techniques, such as, for example, pleats formed in the spacing member 12, twisting or rolling of the spacing member 12 around the elongate member 14, or other similar techniques. The spacing member 12 can also be formed from an elastic material which allows the spacing member 12 to wrap around the elongate member 14 in the closed position, and stretch outwardly from the elongate member 14 in the open position.

A person having ordinary skill in the art will readily appreciate that the spacing member 12 can be disposed in a distal facing direction in the closed position, or can be disposed around or within the elongate member 14 in any manner that allows the device to be inserted through an introducer sheath and then extended into the open position.

Figure 2A:
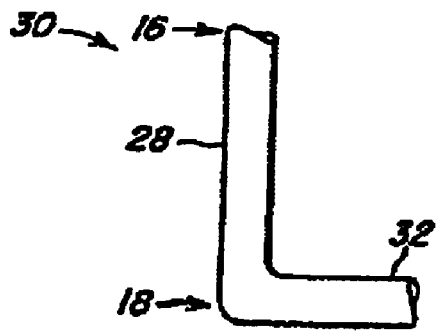
FIG. 2A is a perspective view of an additional embodiment of a spacing member of the present invention formed from a shape memory material.
Figure 2B:
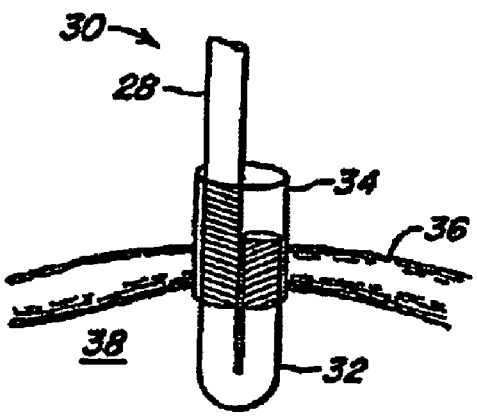
FIG. 2B is a perspective view of the spacing member of FIG. 2A partially inserted into an introducer sheath.
Figure 2C:
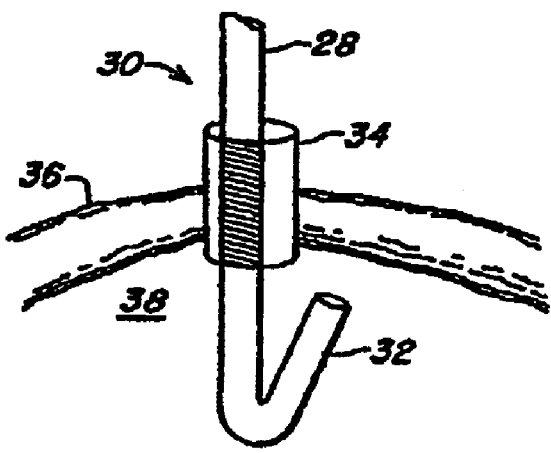
FIG. 2C is a perspective view of the spacing member of FIG. 2A fully inserted through an introducer sheath and into an excision site.
Figure 2D:
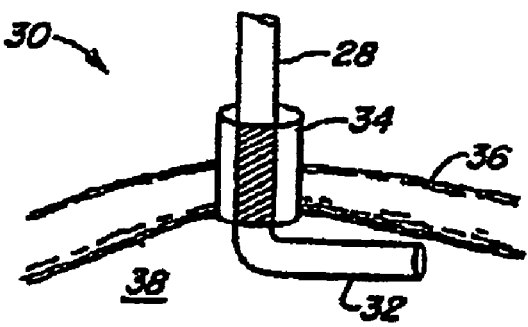
FIG. 2D is a perspective view of the spacing member of FIG. 2A positioned to space a brachytherapy device a distance apart from sensitive tissue proximate to the excision site.

In an alternative embodiment of the separate spacing member 12, the spacing member can be formed integrally with the elongate member 14. By way of non-limiting example, FIG. 2A illustrates a device 30 including spacing member 32 integrally formed on the distal end 18 of an elongate member 28, and being formed from a shape memory material. The shape memory material can be a metal shape memory material such as, for example, those disclosed in U.S. Pat. No. 4,665,906 (which is hereby incorporated by reference), Nitinol® (a commercially available nickel titanium alloy shape memory material), or a composite polymer material having shape memory qualities. The spacing member 32 is shown having an L-shape such that the spacing member 32 extends in a direction substantially perpendicular to the elongate member 28 in its pre-formed position. In use, the introducer sheath 34 holds the spacing member 32 adjacent the elongate member 28 during insertion through the introducer sheath 34, as shown in FIG. 2B. Alternatively, the spacing member 32 can be inserted through an introducer sheath in a substantially straight, fully extended position (not shown). Once the spacing member is fully inserted through the introducer sheath, shown in FIG. 2C, the spacing member 32 resumes (due either to a release of steric constraints or a temperature increase from being placed inside the body) its preformed shape. The apparatus can then be retracted to position the spacing member 32 adjacent the tissue 36 proximate to the excision site 38. While an L-shaped spacing member 32 is illustrated in FIG. 2B, a person of ordinary skill in the art will recognize that various shapes could be used, including a circularly shaped spacing member formable in a plane that is perpendicular to a longitudinal axis of elongate member 28.

Movement of the spacing member 32 according to the present invention between the open and closed positions can be accomplished by a variety of techniques. For example, the apparatus can optionally include an actuating member (not shown), such as a wire, pulley assembly, lever, or similar device, effective to move the spacing member 32 to a position adjacent to the elongate member 28 to allow for insertion of the device through an introducer sheath, and/or to return the spacing member 32 to the open position once inserted. A person having ordinary skill in the art will readily appreciate that a variety of different actuating members can be used to position the spacing member 32 within the excision site 38.

Figure 3A:
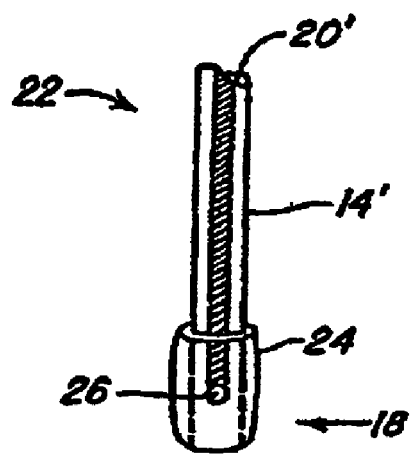
FIG. 3A is a perspective view of another embodiment of a spacing member having an inflatable balloon member according to the present invention.
Figure 3B:
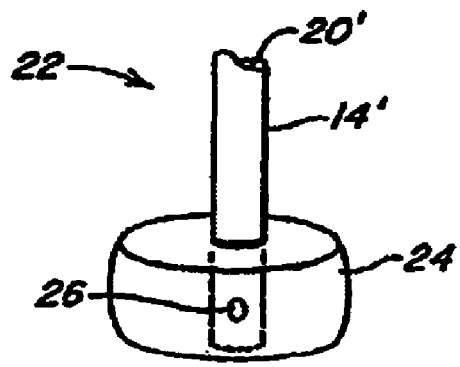
FIG. 3B is a perspective view of the spacing member of FIG. 3A illustrating the balloon member in a partially inflated position.
Figure 3C:
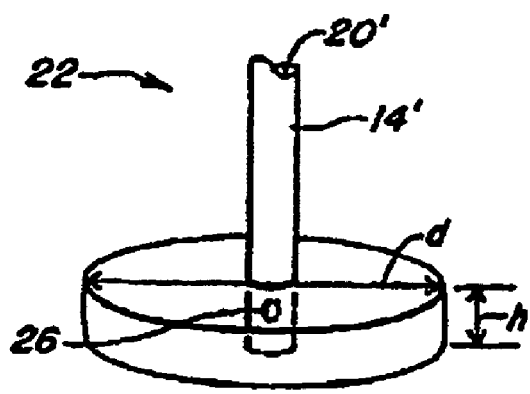
FIG. 3C is a perspective view of the spacing member of FIG. 3A illustrating the balloon member in a fully inflated position.

FIGS. 3A-3C illustrate yet another embodiment of a separate spacing member according to the present invention having a spacing member 24 formed from an inflatable balloon member, and an elongate member 14' similar in purpose and construction to elongate member 14 discussed with respect to FIGS. 1A-1B. The elongate member 14' includes an inner lumen 20' defining a pathway, and a port 26 in communication with the inner lumen 20' for providing air or liquid to inflate the spacing member 24. The elongate member 14' can optionally include an open distal end in communication with a second inner lumen (not shown) for receiving a brachytherapy device.

The spacing member 24 is primarily sealed around the port 26 on the distal end 18 of the elongate member 14', and can include a predetermined shape in its expanded form, shown in FIG. 3C, such that, when inflated, the balloon has a height h which is adapted to provide the desired spacing between the brachytherapy device and the tissue adjacent the excision site. A person having ordinary skill in the art will readily appreciate that the spacing member 24 can have any shape, height h, as well as any diameter d, so long as the spacing member 24 is effective to provide the desired spacing between a brachytherapy device and the tissue adjacent the excision site. The height h and the diameter d of spacing member 24 can be the same or similar to the height h and the diameter d of spacing member 12 described with respect to FIG. 1B. In addition, the height h of spacing member 24 can be selectable during treatment by inflating the balloon to a desired level so as to have the selected height.

Figure 4A:
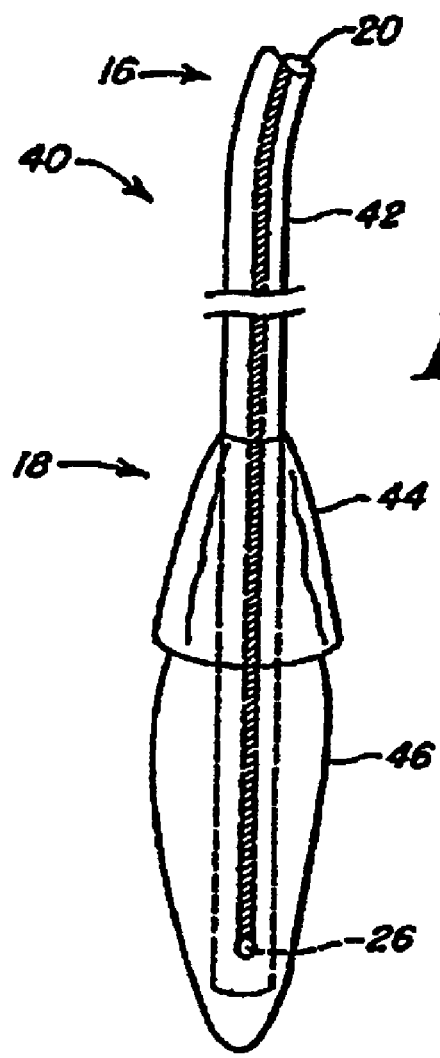
FIG. 4A is a perspective view of yet another embodiment of a spacing member of the present invention having a spacing element disposed on a brachytherapy device.
Figure 4B:
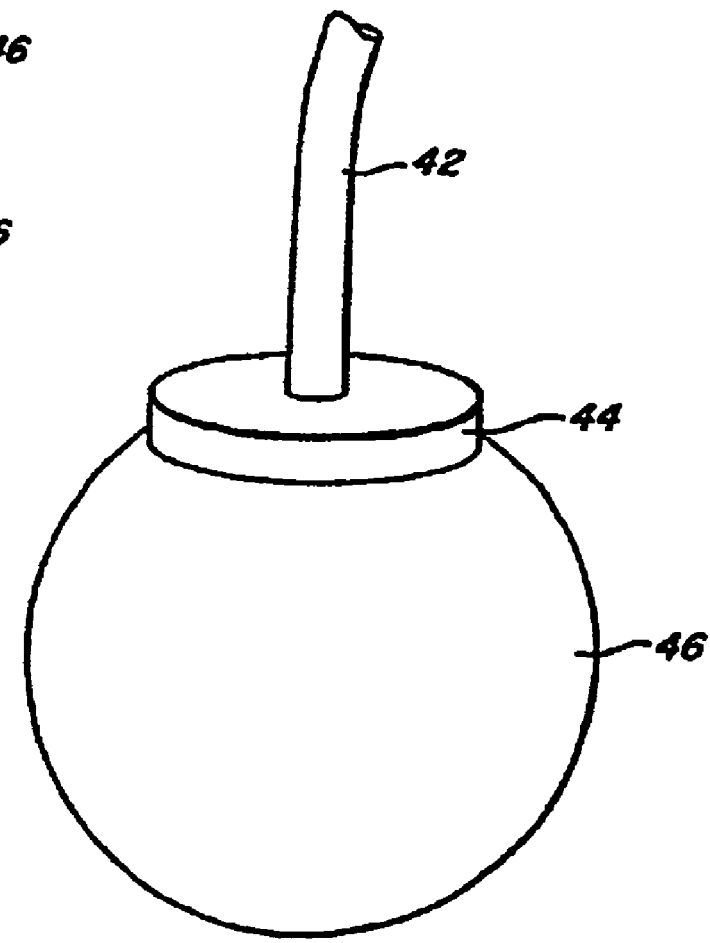
FIG. 4B illustrates the spacing member of FIG. 4A in an open, extended position.

In another embodiment of the present invention, as shown in FIGS. 4A and 4B, the spacing member can be mated to or formed integrally with a brachytherapy device. FIG. 4A illustrates a brachytherapy device 40 having an elongate member 42, a spacing member 44, and an expandable balloon member 46 for receiving a radiation source. The expandable balloon member 46 and the spacing member 44 are disposed on a distal end 18 of the elongate member 42, the spacing member 44 being disposed proximally to the balloon member 46. The elongate member 42 includes at least one inner lumen 20 in communication with a port 26 formed in the distal end 18 of the elongate member 42. The inner lumen 20 is effective to carry a radioactive source and/or an inflation source to the expandable balloon member 46 for inflating the balloon 46, and/or applying radiation to the excision site.

The spacing member 44 is preferably movable between a closed position shown in FIG. 4A, and an open position shown in FIG. 4B. Movement can be accomplished by an actuating member (not shown), or alternatively, the spacing member 44 can be formed from a shape memory material to allow the spacing member 44 to be positioned properly once disposed within the excision site. In one embodiment, the expandable balloon member 46 is effective to move the spacing member 44 to the open position, shown in FIG. 4B, upon expanding the balloon member 46.

In an alternative embodiment, spacing member 24 is a separate balloon member such that first and second balloon member are separately inflatable. Elongate member 42 preferably includes means for carrying separate inflation sources to spacing member 44 and expandable balloon 46. In use, the spacing provided by spacing member 44 can be adjusted by varying the inflation pressure of the spacing member.

Spacing member 44 is similar in purpose and construction to spacing members 12 and 24 described with respect to FIGS. 1A-1B, and 3A-3C. Thus, spacing member 44 can have any shape and size, can be positioned with respect the expandable balloon as needed (proximately, distally, etc.), can be formed integrally with elongate member 42, can be an expandable balloon member disposed on, around, or within elongate member 42, or can be any other type of structure effective for positioning a brachytherapy device at a distance apart from the surface of sensitive tissue proximate to the excision site.

Figure 5A:
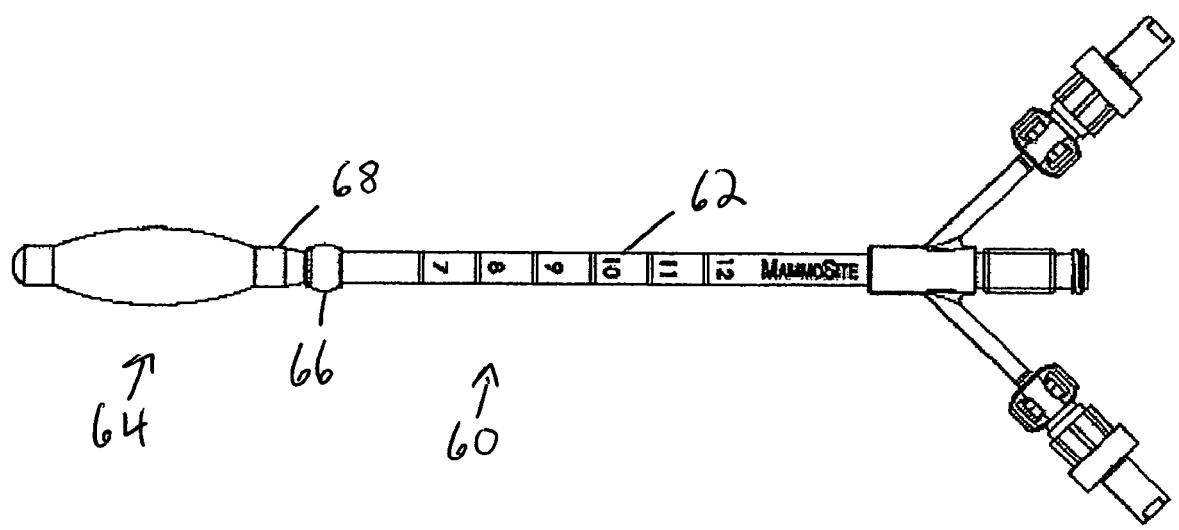
FIG. 5A is a side view of another embodiment of a spacing member of the present invention having a spacing member formed integrally with a balloon member of a brachytherapy device.
Figure 5B:
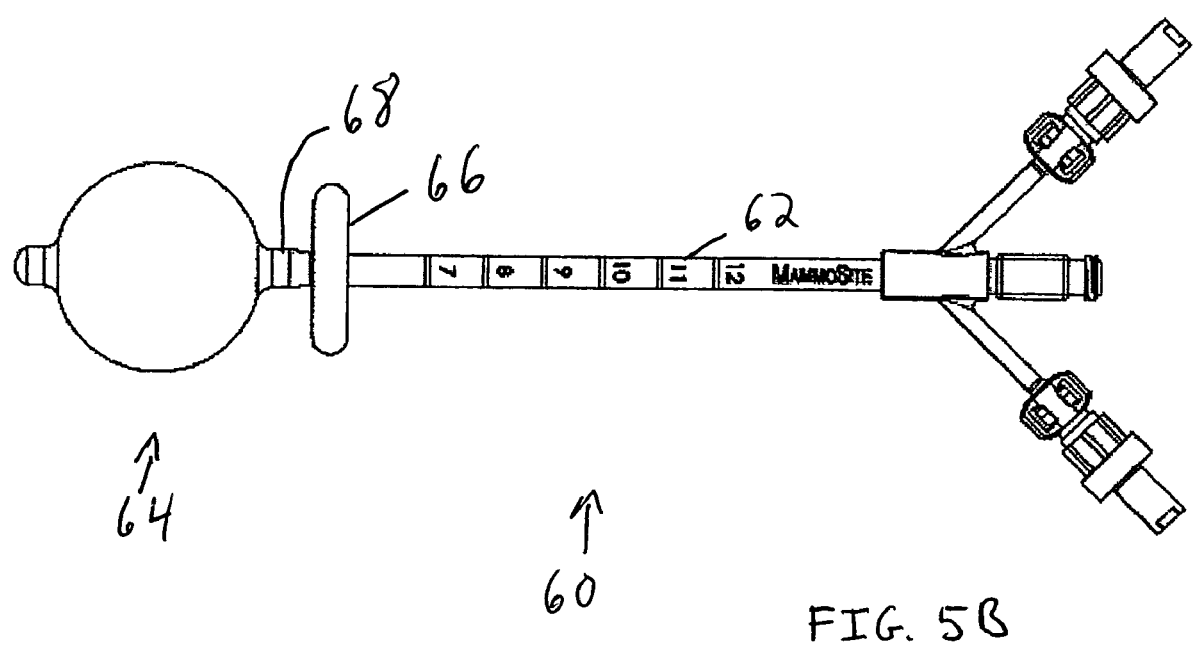
FIG. 5B illustrates the brachytherapy device and spacing member of FIG. 5A in an inflated position.

In one embodiment the spacing member is formed integrally with the expandable balloon member of a brachytherapy device as shown in FIGS. 5A and 5B. The illustrated brachytherapy device 60 represents a typical brachytherapy device including an elongate member 62 and expandable balloon 64 positioned on the distal end thereof. However, the expandable balloon 64 includes a portion that acts as a spacing member 66. FIG. 5B shows the inflated expandable balloon with spacing member 66. Preferably, the distal portion of the expandable balloon receives a radiation source, while spacing member 66 provides additional spacing between the radiation source and adjacent tissue.

When the brachytherapy device is positioned within a resected cavity, the spacing member can protect sensitive tissue adjacent to the cavity entrance. For example, an inflated spacing member 66 can keep skin tissue around an opening to a resected cavity spaced from a radiation source within the brachytherapy device.

In one aspect of the brachytherapy device 60, the inflation medium, used to inflate the expandable balloon and spacing member, can freely travel between the interior of the expandable balloon 64 and spacing member 66. A single inflation lumen can therefore inflate both expandable balloon 64 and spacing member 66. However, in an alternative embodiment, expandable balloon 64 and spacing member 66 are separately inflatable and the brachytherapy device 60 preferably includes separate inflation lumens for independent operation of the expandable balloon 64 and spacing member 66.

A separately inflatable spacing member also allows the user to select different inflation mediums for the expandable balloon and the spacing member. For example, expandable balloon 64 could be inflated with generally radiation transparent fluid, such as saline, while spacing member 66 could be inflated with a radiation blocking fluid, such as contrast fluid. As a result, the spacing member could reduce radiation dosage by spacing adjacent tissue and blocking radiation emissions.

Figure 6A:
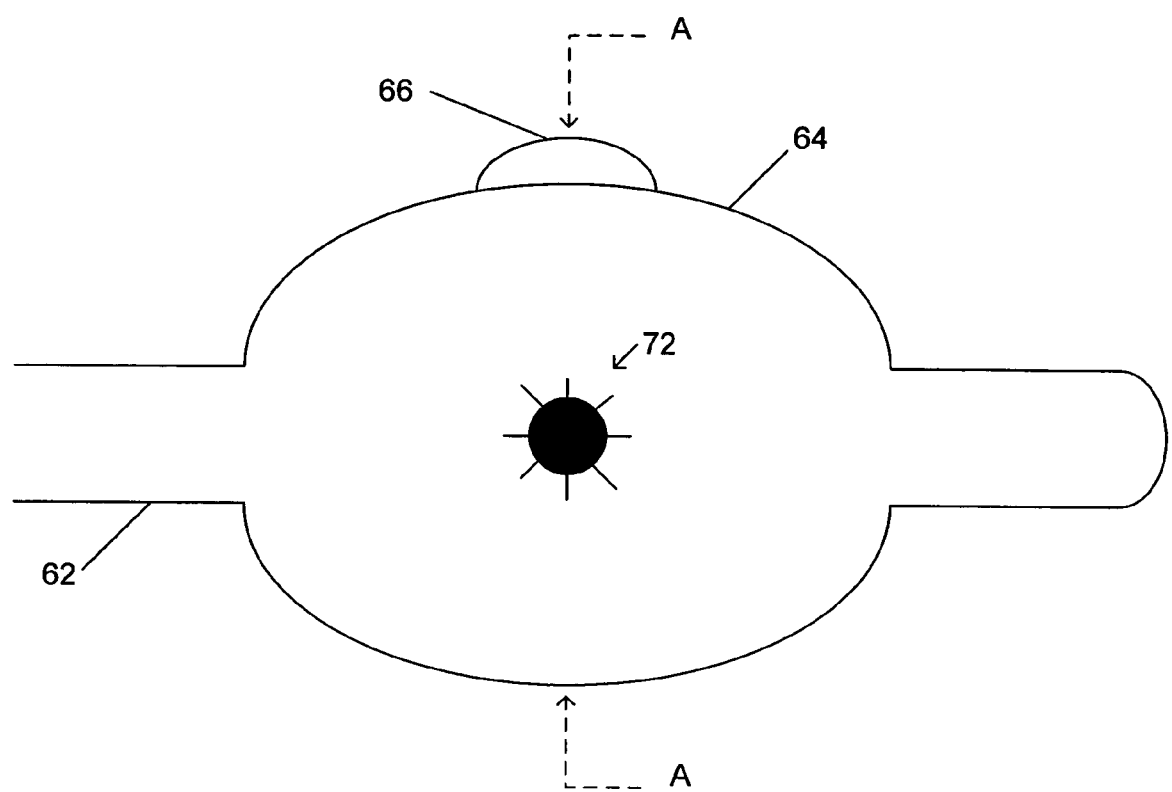
FIG. 6A illustrates a side view of another embodiment of the present invention including a expandable balloon with spacing member.
Figure 6B:
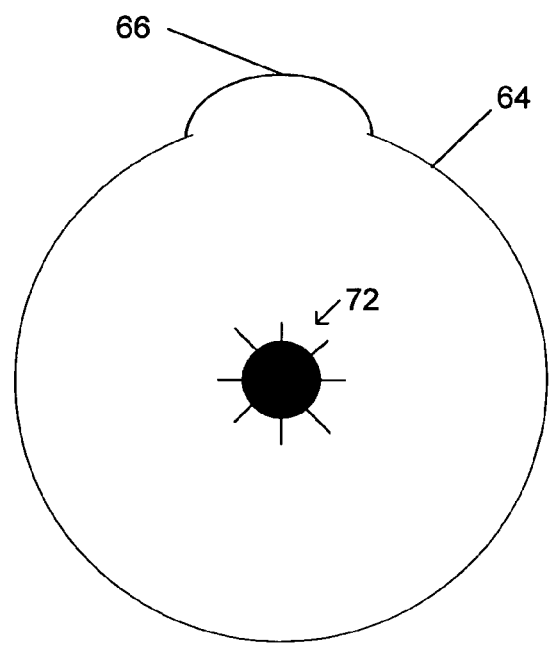
FIG. 6B is a cut-away view of FIG. 6A along the line A-A.

A variety of other brachytherapy balloons that include integrally formed spacing members are also contemplated. FIG. 6A illustrates a brachytherapy device with elongate member 62 and expandable balloon member 64 including spacing member 66 provided by an asymmetric bulge in the expandable balloon. The outwardly positioned asymmetric spacing area increases the distance between radiation source 72 and tissue adjacent to spacing member 66. FIG. 6B illustrates a cross section of the device of FIG. 6A cut perpendicular to the axis of the elongate member along the line A-A. The cross section illustrates the nonconcentric circumference of the expandable balloon created by spacing member 66. Preferably, expandable balloon 64 includes a generally uniform shape and cross section, with the exception of spacing member 66. As a result, the tissue spaced by the spacing member receives a radiation dose less than an isodose received by tissue adjacent to other portions of the expandable balloon.

In another embodiment, the expandable surface member can include an asymmetric shape such that the asymmetric spacing area provides reduced spacing between tissue adjacent to the asymmetric spacing area and a radiation source position within the expandable balloon. One such exemplary asymmetric spacing area includes an inwardly positioned asymmetric spacing area that does not conform to the generally uniform shape of the expandable surface member. The tissue spaced by the spacing member receives a radiation dose more than an isodose received by the tissue adjacent to the other portions of the expandable balloon.

Creation of an integral spacing member in the expandable balloon of a brachytherapy device can be achieved in a variety of ways. In one embodiment, the expandable balloon includes an area of increased (or decreased) thickness such that as the balloon expands, the area of increased thickness expands to a lesser (or greater) extent. The resulting balloon has an asymmetric shape that provides an area of increased spacing between a radiation source and adjacent tissue. For example, area 68 in FIGS. 5A and 5B could be an area of increased thickness such that as expandable balloon 64 expands, area 68 expands at a slower rate. The resulting expandable balloon includes proximal and distal lobes. With a radiation source placed in the distal lobe of the expandable balloon, the proximal lobe provides a spacing member such that tissue proximate to the expandable member is spaced from the radiation source.

Variable thickness expandable balloon walls can be achieved in a number of ways. For example, during the construction of molded balloons (e.g., molded silicon balloons) the mold thickness can be varied. In other manufacturing processes, such as blow-molding of polyurethane, varying pressure and/or temperature differential on one area of the mold, using a shaped mold cavity, and/or selectively positioning the extrusion hole can create variations in the mold. Other variations in the primary manufacturing steps which create variations in the balloon wall thickness are also included within the scope of the invention.

The wall thickness of brachytherapy balloons with variable wall thickness preferably remains above certain minimums to retain sufficient material strength and shape control. These preferred minimums will vary depending on the choice in construction material. As an example, the minimum thickness for a balloon constructed primarily from silicon is about 0.01 inches, and even more preferably not below 0.018 inches. Similarly, the variation in wall thickness necessary to produce variations in shape also depends on the construction material. For silicon balloons, the variation in wall thickness between adjacent portions of the expandable balloon is preferably in the range of about 0.001 to 0.04 inches, and even more preferably in the range of about 0.02 to 0.035 inches.

Other ways of constructing an integrally formed spacing member in an expandable brachytherapy balloon are also contemplated. In one embodiment, balloon shape can be controlled with a constraining sleeve positioned around the balloon. The sleeve preferably controls the rate of expansion for a portion of the balloon such as the balloon inflates, the sleeve constrains the amount of expansion over a portion of the balloon. Thus, when expanded the balloon includes an unconstrained area having relatively more spacing from a radiation source. For example, area 68 in FIGS. 5A and 5B could be a constraining sleeve wrapped around expandable balloon 62.

The expandable balloon can be constructed from a variety of materials including plastic, metal, composite materials, and the like. In addition, the materials can have a variety of properties depending on the use of the expandable balloon. For example, where the balloon does not require elastic properties, the expandable balloon can be constructed from materials having minimal, or no, elasticity. Radiopaque materials, or radiopaque coating are also contemplated on all or a portion of the spacing member. Suitable radiopaque materials include, for example, barium, tungsten, bismuth, tantalum and tin.

The spacing member of the invention can be used in the treatment of a variety of malignant tumors, and is especially useful in the treatment of brain and breast tumors. Surgery and radiation therapy are the standard treatments for malignant tumors. The goal of surgery is to remove as much of the tumor as possible without damaging vital tissue. The ability to remove the entire malignant tumor is limited by its tendency to infiltrate adjacent normal tissue. Partial removal reduces the amount of tumor to be treated by radiation therapy and, under some circumstances, such as with brain tumors, helps to relieve symptoms by reducing pressure on the brain.

A common method for treating these and other malignancies begins by surgical resection of a tumor site to remove at least a portion of the cancerous tumor and create a resection cavity. Following tumor resection, but prior to closing the surgical site, the surgeon intra-operatively places a brachytherapy catheter apparatus into the tumor resection cavity. In some instances, the brachytherapy catheter apparatus can be implanted or inserted into the tumor resection cavity up to several months after surgery is complete. The brachytherapy catheter can be loaded with a radiation source either during surgery or following recovery from surgery as medically appropriate. The radioactive source dwells in the catheter until the prescribed dose of radiotherapy is delivered, or the radiation source can be inserted for prescribed amounts of time on a daily or other scheduled basis until the prescribed dosage has been achieved. The radiation source is then retrieved and the catheter is removed. The radiation treatment may end upon removal of the brachytherapy apparatus, or the brachytherapy may be supplemented by further doses of radiation supplied externally.

The spacing member described herein can be useful for positioning the brachytherapy apparatus at a distance apart from the sensitive tissue proximate to the excision site. The spacing member can be inserted through the same surgical entry site as the brachytherapy apparatus, or alternatively can be inserted through a separate entry site. A person having ordinary skill in the art will appreciate that a variety of different methods can be used for positioning a brachytherapy device at a distance apart from the outer surface of the tissue adjacent the excision site.

By way of non-limiting example, FIGS. 7A-7D illustrate a spacing member 10, as described with respect to FIGS. 1A-1B, in use with a brachytherapy device 50 to treat a breast cancer. As an initial step, surgical access to the site of the cancerous tumor is created and the bulk of the tumor is surgically resected. Spacer 10 and brachytherapy device 50 can then be deployed to treat remaining cancer cells while protecting sensitive tissue such as skin 36.

Brachytherapy device 50, comprising generally an inflatable balloon 46 for housing a radiation source disposed on the distal end of catheter 56, is inserted (FIG. 7A) into a resection cavity 38 through surgical entry site 52, which may be the surgical approach through which the tumor was resected or an opening created specifically for deployment of brachytherapy device 50. Spacing member 10 can be inserted (FIG. 7B) into resection cavity 38 through a separate entry site 54 through introducer sheath 34. A person of ordinary skill in the art will recognize that spacer 10 and brachytherapy device 50 can be inserted into resection cavity 38 in any order, and that spacer 10 can be inserted through either separate entry site 54 or through surgical entry site 52 depending on the configuration of spacer 10. For example, spacing member 30 of FIGS. 2A-2D, because of its configuration, could be inserted through either surgical entry site 52 or separate entry site 54. In the example illustrated in FIGS. 7A-7D, separate entry site 54 is used.

Figure 7C:
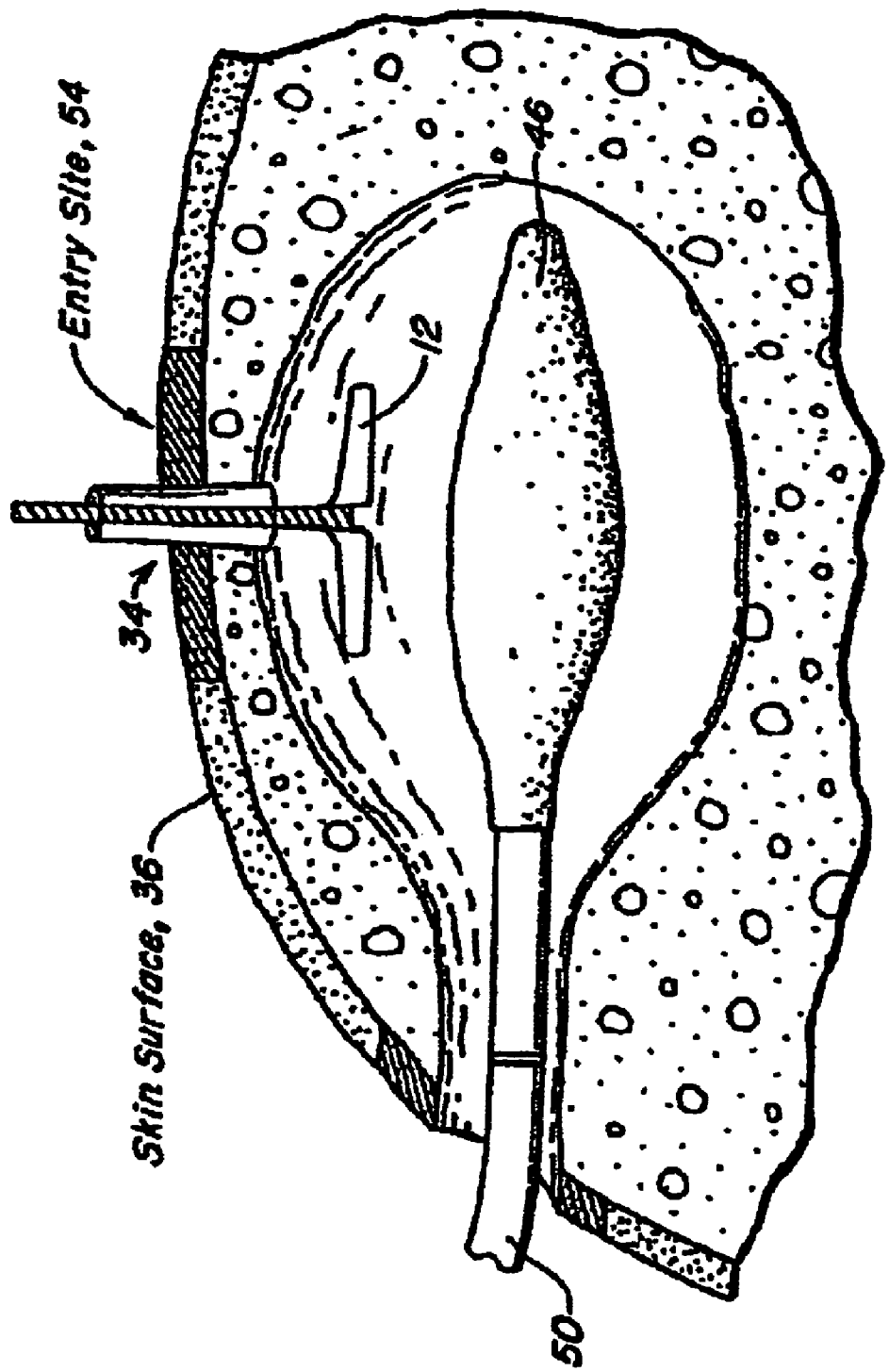
FIG. 7C illustrates the spacing member of FIG. 5A fully inserted into the surgical excision site.

Once spacing member 10 is fully inserted into resection cavity 38, spacing member 12 is moved to its open position, as shown in FIG. 7C. Spacing member 10 can then be retracted, or can be pushed against an outer surface of the resection cavity 38 upon inflation of the balloon member 46 of the brachytherapy device 50. Introducer sheath 34 can optionally be removed, leaving spacing member 10 abutting an outer surface of resection cavity 38, as shown in FIG. 7D, and maintaining the brachytherapy device at the desired spacing apart from skin 36.

Figure 8:
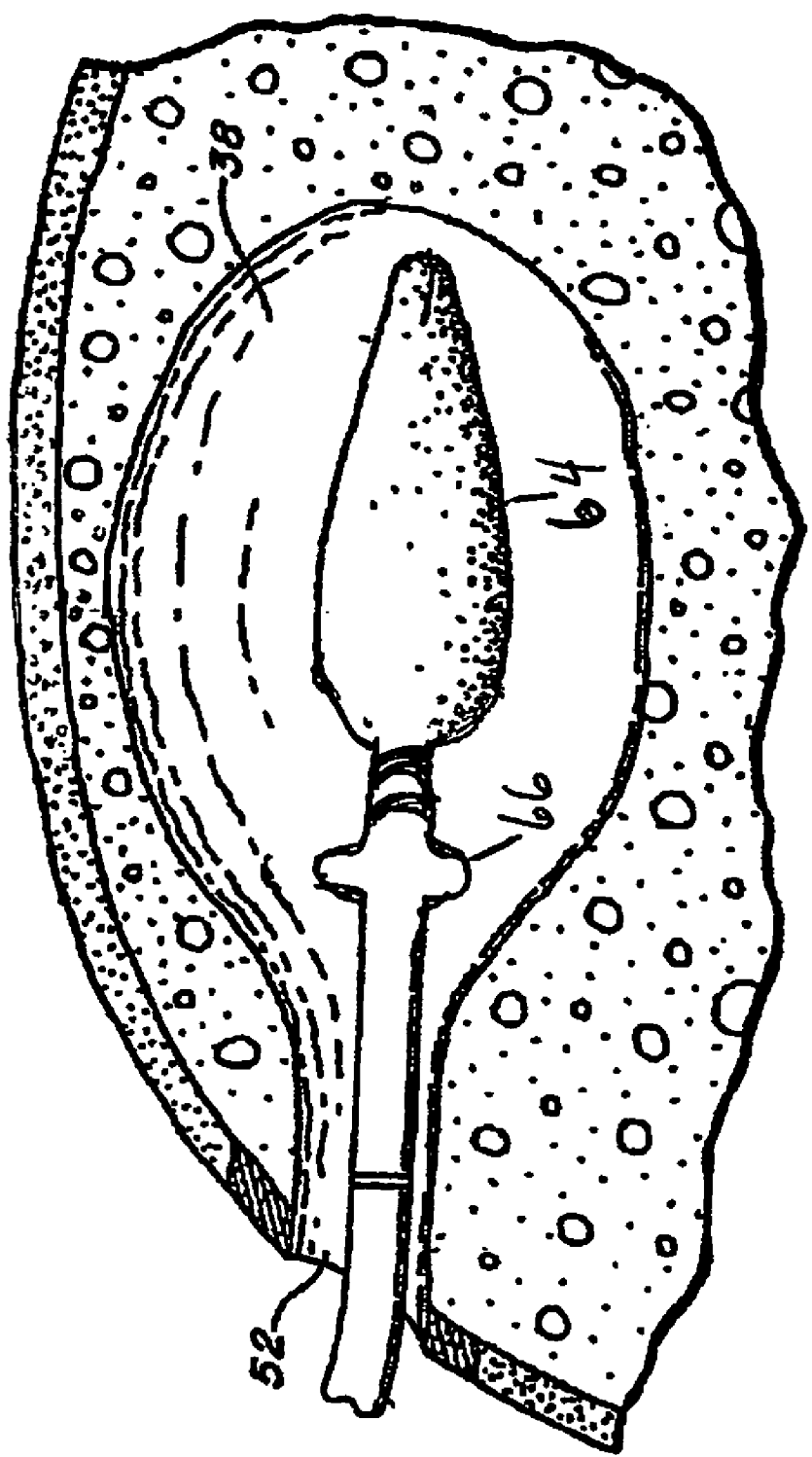
FIG. 8 illustrates a brachytherapy device disposed within a surgical excision site including a spacing member according to one embodiment of the present invention.

In some cases, the spacing member must be inserted through the same entry site as the brachytherapy device as the spacer is connected to the brachytherapy device. FIG. 8 illustrates the brachytherapy device 60 of FIGS. 5A and 5B positioned in resection cavity 38 and ready for inflation. Once inflated, spacing member 66 can provide spacing to sensitive tissue, particularly around surgical entry site 52. The brachytherapy devices of FIGS. 4A, 4B, 6A, and 6B can be similarly inserted into resection cavity 38 and used in the same manner.

It will be understood that the foregoing is only illustrative of the principles of the invention, and that various modifications can be made by those skilled in the art without departing from the scope and spirit of the invention, including, but not limited to, combinations of elements from different embodiments found herein. All references cited herein are expressly incorporated by reference in their entirety.

What is claimed is:

1. A brachytherapy device, comprising:
   an insertion member having a proximal end and a distal end; and
   an expandable surface member disposed on the distal end of the insertion member and effective to receive a radiation source for treating target tissue surrounding a surgical excision site, the expandable surface member including an area of diminished thickness such that applying inflation pressure to the expandable surface member expands the area of diminished thickness at a greater rate than adjacent portions of the expandable surface member, and upon inflation creates an asymmetrically shaped expandable surface member adapted to space tissue from a radiation source.

2. The device of claim 1, wherein the cross section of the expandable surface member is asymmetrical.

3. A brachytherapy device, comprising:
   an insertion member having a proximal end and a distal end; and
   an expandable surface member disposed on the distal end of the insertion member and effective to receive a radiation source for treating target tissue surrounding a surgical excision site, the expandable surface member including an area of increased thickness such that applying inflation pressure to the expandable surface member expands the area of increased thickness at a reduced rate compare with adjacent portions of the expandable surface member, and upon inflation creates an asymmetrically shaped expandable surface member adapted to space tissue from a radiation source.

4. The brachytherapy device of claim 3, wherein the expandable surface includes a proximal spacing area when expanded.

5. The brachytherapy device of claim 3, wherein the expandable surface includes a distal spacing area when expanded.

6. A brachytherapy device, comprising:
   an insertion member having a proximal end and a distal end;
   a first expandable surface member disposed on the distal end of the insertion member and effective to receive a radiation source for treating target tissue surrounding a surgical excision site; and
   a second expandable surface member disposed on the distal end of the insertion member proximate to the first expandable surface member and effective to space tissue from the first expandable surface member;
   wherein the first and second expandable surface members are formed by a sleeve disposed around the circumference of the insertion member.

7. The device of claim 6, wherein the second expandable surface member is separately inflatable.

8. The device of claim 6, wherein varying the inflation pressure of the second expandable surface member adjusts the spacing provided by the second expandable surface member.

9. A brachytherapy device, comprising:
   an insertion member having a proximal end and a distal end;
   an expandable surface member disposed on the distal end of the insertion member, the expandable surface member including a first proximal lobe and a second distal lobe formed by a sleeve disposed on the expandable surface member;
   the first proximal lobe positioned proximate to the distal lobe and effective to space tissue from the distal lobe; and
   the second distal lobe effective to receive a radiation source for treating target tissue surrounding a surgical excision site.

10. The device of claim 9, wherein the expandable surface member is mated to the insertion member between the first proximal lobe and the second distal lobe.

11. The device of claim 9, wherein the expandable surface member includes an area of increased thickness between the lobes.

* * * * *